(12) United States Patent
Liu

(10) Patent No.: US 11,246,343 B2
(45) Date of Patent: Feb. 15, 2022

(54) ELECTRONIC CIGARETTE

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 267 days.

(21) Appl. No.: 16/697,154

(22) Filed: Nov. 26, 2019

(65) Prior Publication Data

US 2021/0093019 A1    Apr. 1, 2021

(30) Foreign Application Priority Data

Sep. 26, 2019 (CN) .......................... 201910918712.4
Sep. 26, 2019 (CN) .......................... 201921617585.6

(51) Int. Cl.
*A24F 13/00* (2006.01)
*A24F 17/00* (2006.01)
*A24F 25/00* (2006.01)
*A24F 40/40* (2020.01)

(52) U.S. Cl.
CPC ..... *A24F 40/40* (2020.01); *A61M 2205/8206* (2013.01)

(58) Field of Classification Search
CPC .. A24F 40/10; A24F 40/40; A61M 2205/8206
See application file for complete search history.

(56) References Cited

U.S. PATENT DOCUMENTS

| | | | |
|---|---|---|---|
| 10,412,785 B1 * | 9/2019 | Schwartz | ................ H05B 3/16 |
| 2016/0007648 A1 * | 1/2016 | Sutton | .................... A24F 13/06 |
| | | | 131/187 |
| 2018/0303166 A1 * | 10/2018 | Qiu | ....................... A61M 15/06 |
| 2019/0239568 A1 * | 8/2019 | Ouyang | ............... A61M 15/06 |
| 2020/0245693 A1 * | 8/2020 | Kleizo | .................. H01H 13/52 |
| 2021/0219609 A1 * | 7/2021 | Rado | ...................... A24F 40/48 |

* cited by examiner

*Primary Examiner* — Abdullah A Riyami
*Assistant Examiner* — Thang H Nguyen
(74) *Attorney, Agent, or Firm* — Matthias Scholl P.C.; Matthias Scholl

(57) ABSTRACT

An electronic cigarette, including: an atomization assembly and a battery assembly. The atomization assembly is disposed on the battery assembly. The atomization assembly includes a first cover; a silicone sleeve; a mouthpiece; a first silicone ring; a steel bushing; a second cover; a second silicone ring; an e-liquid container; a third silicone ring; a filler plug; an atomization unit. The battery assembly includes a positive joint; a first spring; a first insulation ring; a negative pole; a first fixed part; a second insulation ring; a seal ring; a second fixed part; a fastener; a control plate; a position limiter; a battery; a support; a power button; a housing; a second spring; and a buckle. The first cover includes a cavity and the silicone sleeve is disposed in the cavity. The first cover is removably disposed on the mouthpiece. The first silicone ring is sheathed on the mouthpiece.

1 Claim, 5 Drawing Sheets

ELECTRONIC CIGARETTE

CROSS-REFERENCE TO RELATED APPLICATIONS

Pursuant to 35 U.S.C. § 119 and the Paris Convention Treaty, this application claims foreign priority to Chinese Patent Application No. 201910918712.4 filed Sep. 26, 2019 and to Chinese Patent Application No. 201921617585.6 filed Sep. 26, 2019. The contents of all of the aforementioned applications, including any intervening amendments thereto, are incorporated herein by reference. Inquiries from the public to applicants or assignees concerning this document or the related applications should be directed to: Matthias Scholl P C., Attn.: Dr. Matthias Scholl Esq., 245 First Street, 18th Floor, Cambridge, Mass. 02142.

BACKGROUND

The disclosure relates to an electronic cigarette.

Electronic cigarettes atomize nicotine-containing e-liquid.

Conventional electronic cigarettes include an atomization assembly and a battery assembly which are fixedly connected to each other. This leads to the difficulty of replacing either assembly separately.

SUMMARY

The disclosure provides an electronic cigarette.

The electronic cigarette comprises an atomization assembly and a battery assembly. The atomization assembly is disposed on the battery assembly.

The atomization assembly comprises a first cover; a silicone sleeve; a mouthpiece; a first silicone ring; a steel bushing; a second cover; a second silicone ring; an e-liquid container; a third silicone ring; a filler plug; an atomization unit.

The battery assembly comprises a positive joint; a first spring; a first insulation ring; a negative pole; a first fixed part; a second insulation ring; a seal ring; a second fixed part; a fastener; a control plate; a position limiter; a battery; a support; a power button; a housing; a second spring; and a buckle.

The first cover comprises a cavity and the silicone sleeve is disposed in the cavity; the first cover is removably disposed on the mouthpiece; the first silicone ring is sheathed on the mouthpiece; the steel bushing is sheathed on the mouthpiece; the mouthpiece is disposed on the second cover; the second silicone ring is sheathed on the second cover; the second cover is disposed on the e-liquid container; the atomization unit is directly connected to the e-liquid container; the third silicone ring is disposed between the e-liquid container and the atomization unit; and the filler plug is disposed on the atomization unit.

The control plate comprises positive and negative electrodes respectively connected to positive and negative electrodes of the battery; the control plate and the battery are disposed on the support; the position limiter is disposed in the support; the first spring is disposed on the positive joint; the positive joint is sheathed on the first insulation ring; the positive joint and the first insulation ring are disposed in the negative pole; the first fixed part is disposed on the negative pole; the seal ring is sheathed on the negative pole; the second insulation ring is sheathed on the second fixed part; the second insulation ring and the second fixed part are disposed on the positive joint; the positive joint is disposed on the support; the positive and negative electrodes of the control plate are connected to the positive joint and the negative pole, respectively; the power button is disposed on the housing; the second spring is disposed in a cavity of the buckle; the second spring and the buckle are disposed in the housing; and the fastener is disposed on the support; and the support is disposed in the housing.

DETAILED DESCRIPTION

To further illustrate, embodiments detailing an electronic cigarette are described below. It should be noted that the following embodiments are intended to describe and not to limit the disclosure.

Figure 1:
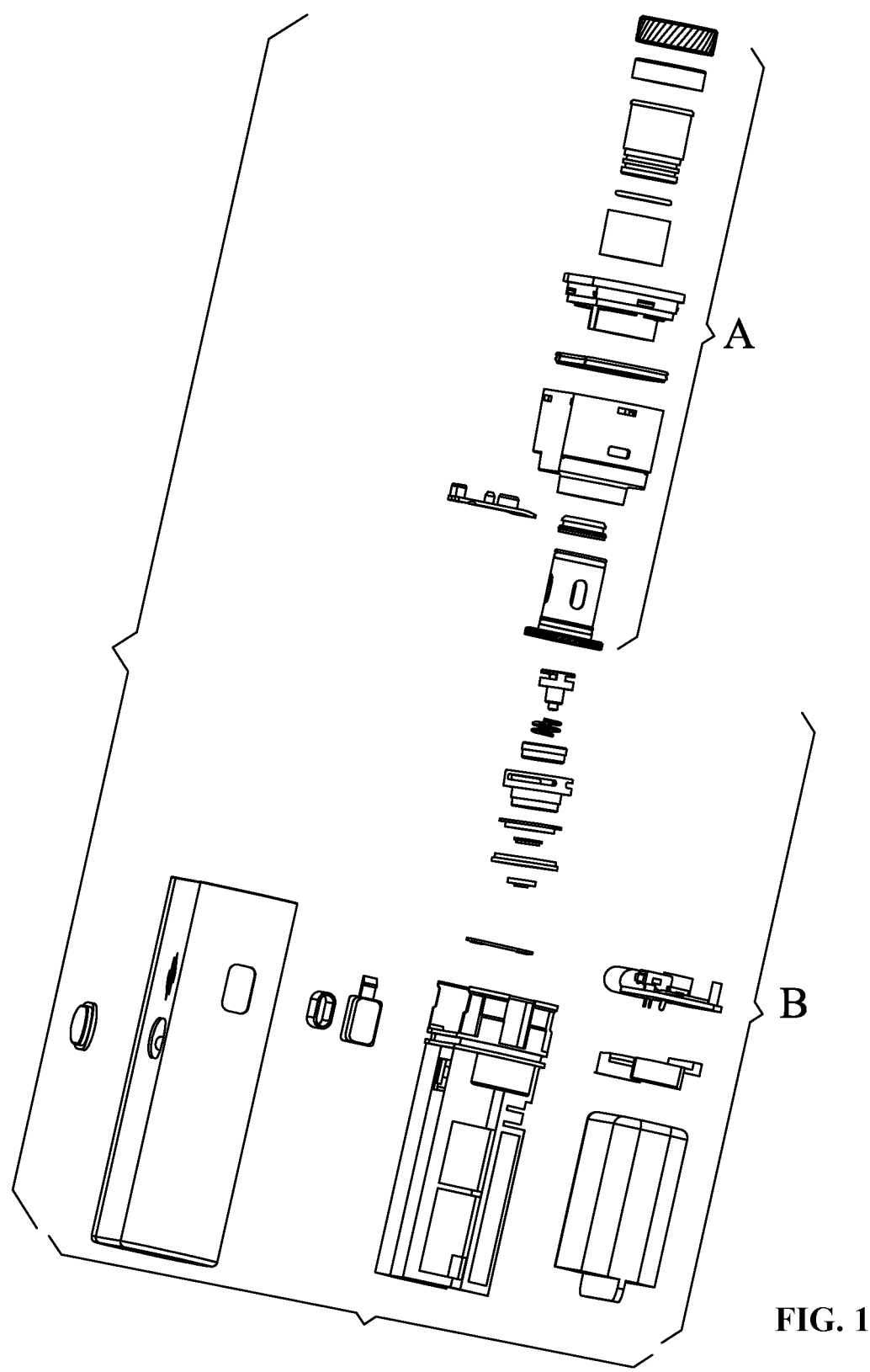
FIG. 1 is an exploded view of an electronic cigarette according to one embodiment of the disclosure.
Figure 2:
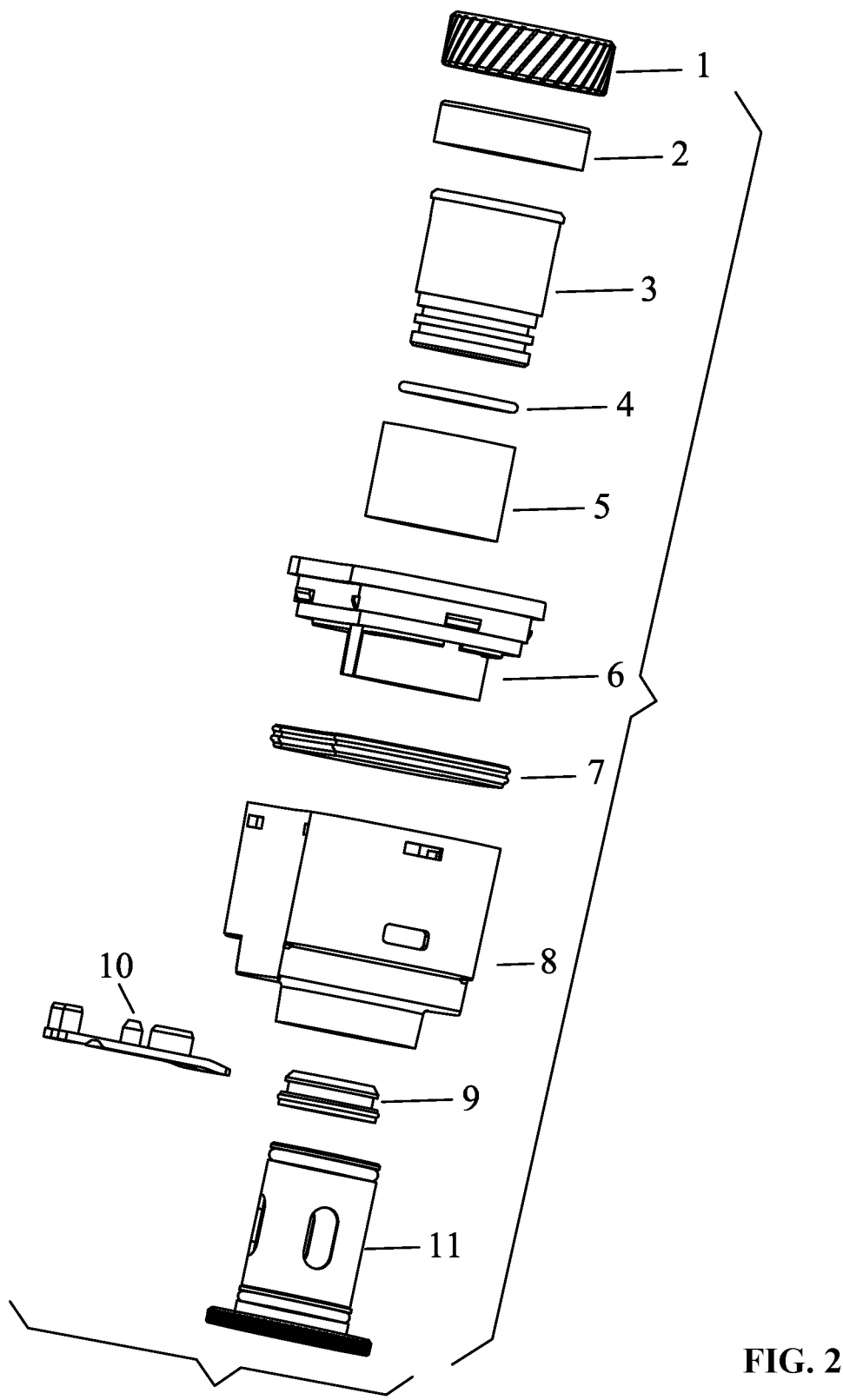
FIG. 2 is an exploded view of an atomization assembly of an electronic cigarette in FIG. 1.
Figure 3:
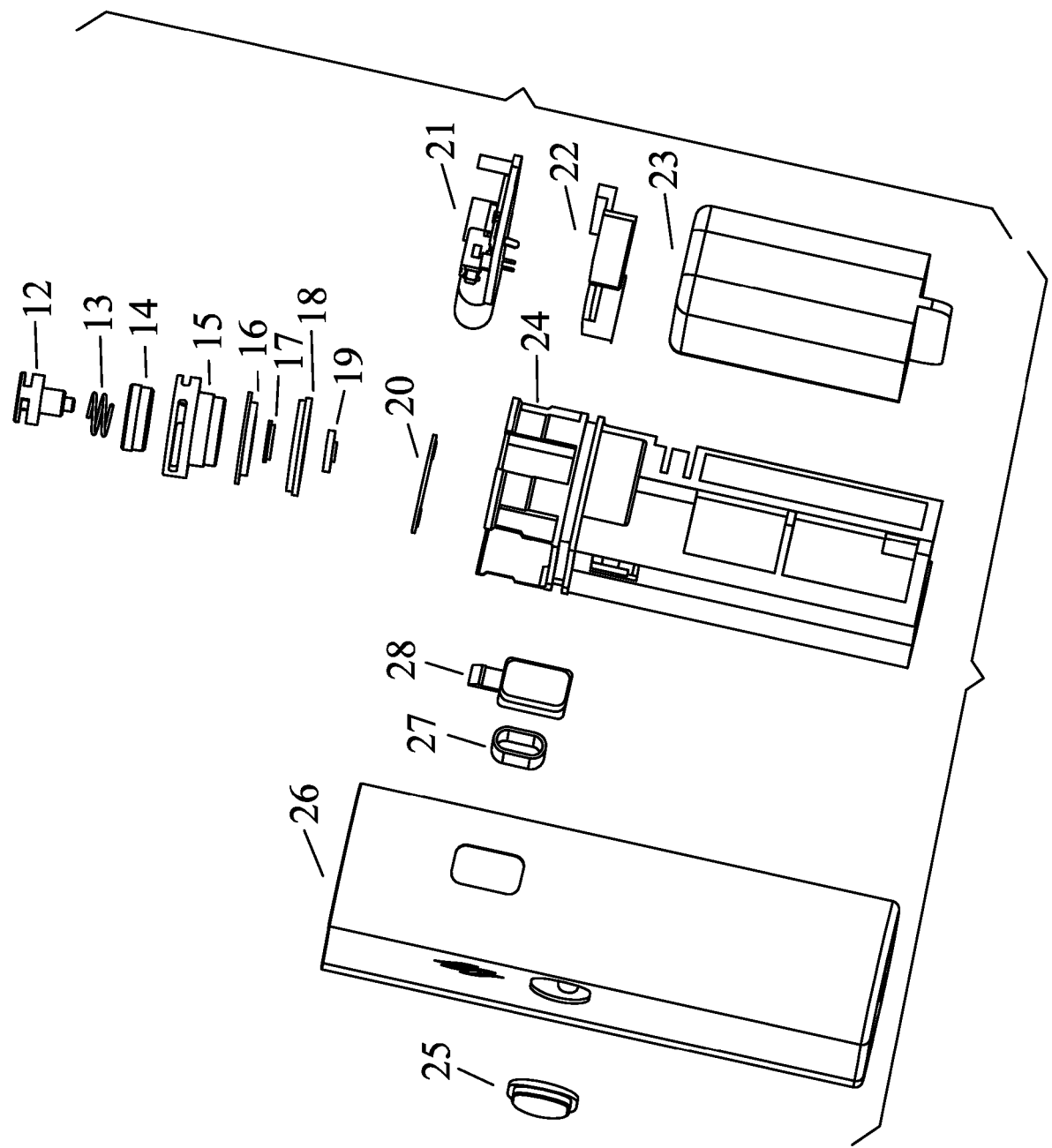
FIG. 3 is an exploded view of a battery assembly of an electronic cigarette in FIG. 1.
Figure 4:
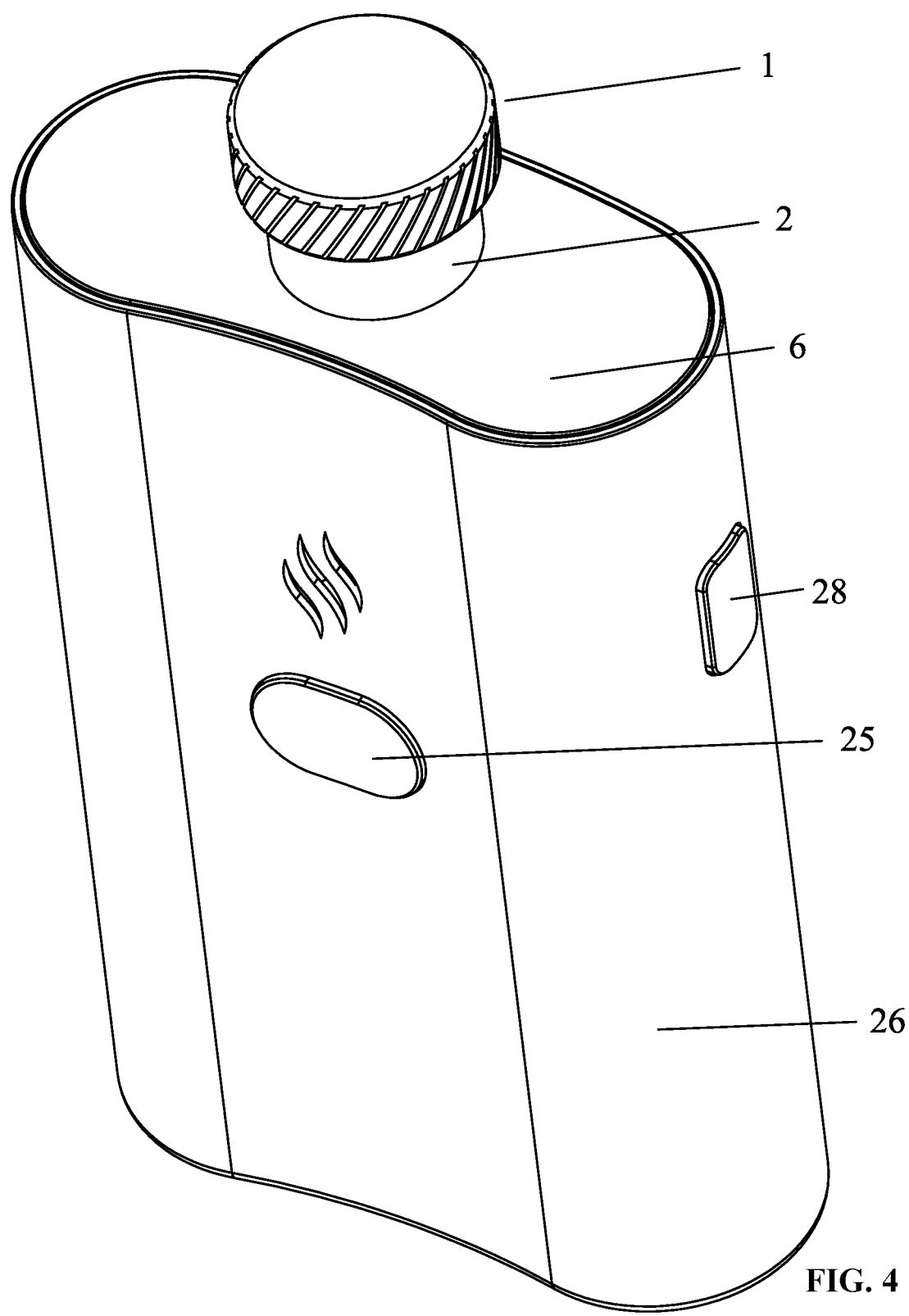
FIG. 4 is a stereogram of an electronic cigarette according to one embodiment of the disclosure.
Figure 5:
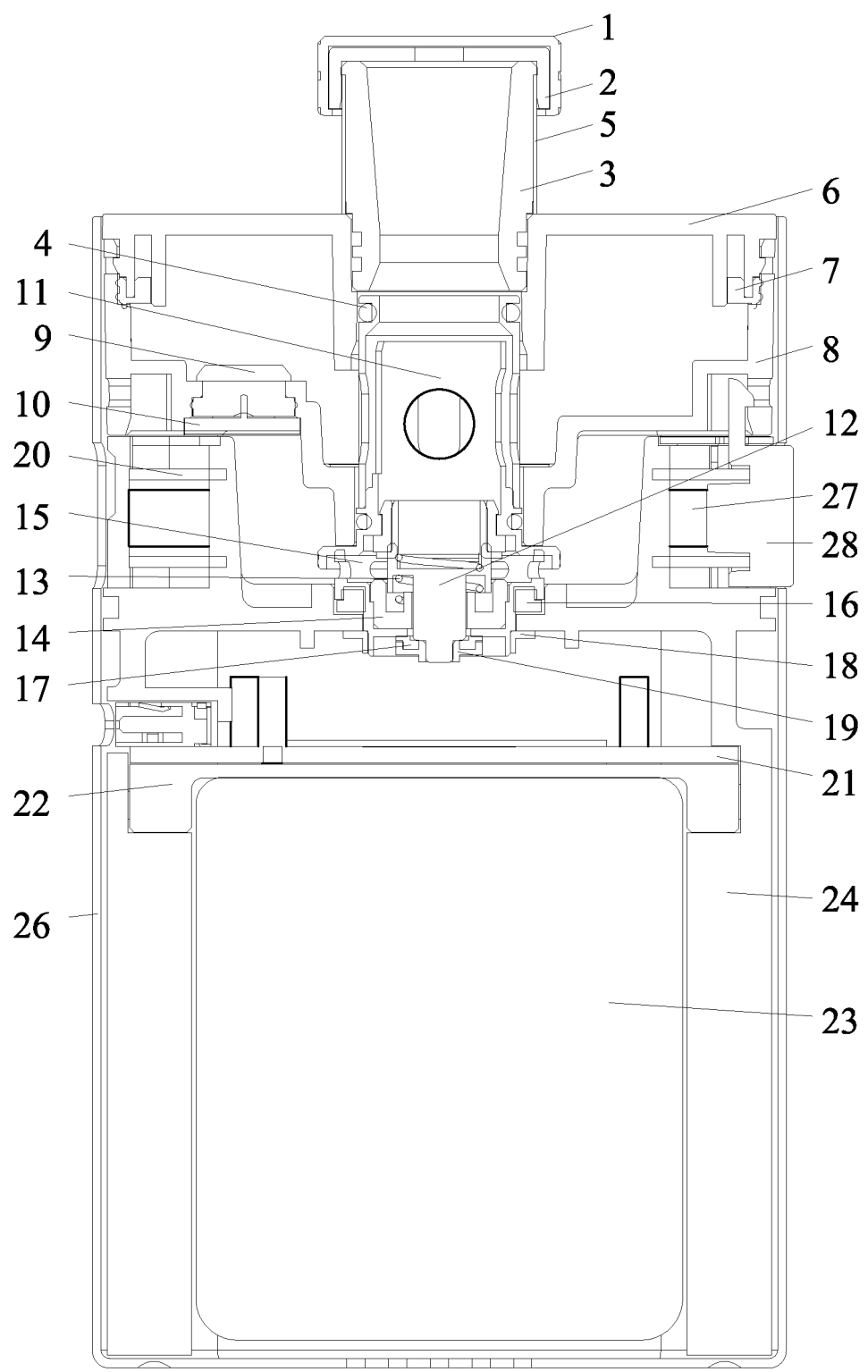
FIG. 5 is a sectional view of an electronic cigarette according to one embodiment of the disclosure.

As shown in FIGS. 1-5, an electronic cigarette comprises an atomization assembly A and a battery assembly B. The atomization assembly A is disposed on the battery assembly B. The atomization assembly A comprises a first cover 1; a silicone sleeve 2; a mouthpiece 3; a first silicone ring 4; a steel bushing 5; a second cover 6; a second silicone ring 7; an e-liquid container 8; a third silicone ring 9; a filler plug 10; an atomization unit 11. The battery assembly comprises a positive joint 12; a first spring 13; a first insulation ring 14; a negative pole 15; a first fixed part 16; a second insulation ring 17; a seal ring 18; a second fixed part 19; a fastener 20; a control plate 21; a position limiter 22; a battery 23; a support 24; a power button 25; a housing 26; a second spring 27; and a buckle 28.

The first cover 1 comprises a cavity and the silicone sleeve 2 is disposed in the cavity; the first cover 1 is removably disposed on the mouthpiece 3; the first silicone ring 4 is sheathed on the mouthpiece 3; the steel bushing 5 is sheathed on the mouthpiece 3; the mouthpiece 3 is disposed on the second cover 6; the second silicone ring 7 is sheathed on the second cover 6; the second cover 6 is disposed on the e-liquid container 8; the atomization unit 11 is directly connected to the e-liquid container 8; the third silicone ring 9 is disposed between the e-liquid container 8 and the atomization unit 11; and the filler plug 10 is disposed on the atomization unit 11.

The control plate 21 comprises positive and negative electrodes respectively connected to positive and negative electrodes of the battery 23; the control plate 21 and the battery 23 are disposed on the support 24; the position limiter 22 is disposed in the support 24; the first spring 13 is disposed on the positive joint 12; the positive joint 12 is sheathed on the first insulation ring 14; the positive joint 12 and the first insulation ring 14 are disposed in the negative pole 15; the first fixed part 16 is disposed on the negative pole 15; the seal ring 18 is sheathed on the negative pole 15; the second insulation ring 17 is sheathed on the second fixed part 19; the second insulation ring 17 and the second fixed part 19 are disposed on the positive joint 12; the positive joint 12 is disposed on the support 24; the positive and negative electrodes of the control plate 21 are connected to the positive joint 12 and the negative pole 15, respectively; the power button 25 is disposed on the housing 26; the second spring 27 is disposed in a cavity of the buckle 28; the second spring 27 and the buckle 28 are disposed in the housing 26; and the fastener 20 is disposed on the support 24; and the support 24 is disposed in the housing 26.

The atomization assembly is connected to the battery assembly via the buckle 28. The second spring 27 is disposed in the cavity of the buckle 28; press the second spring 27, the buckle 28 can be released and eject. Thus, it is easy to separate the atomization assembly from the battery assembly.

In this example, the volume of the e-liquid container 8 is 5.6 mL, which is larger than that of conventional e-liquid containers, thus extending the usage time of the electronic cigarette.

The filler plug 10 comprises environmentally friendly materials, such as silicone gel, and produces no toxic substances even contacting the e-liquid, thus ensuring the user experience.

The battery of the disclosure has a high capacity, can output high current, so that the electronic cigarette can produce much vapor.

It will be obvious to those skilled in the art that changes and modifications may be made, and therefore, the aim in the appended claims is to cover all such changes and modifications.

What is claimed is:

1. A device, comprising: an atomization assembly and a battery assembly; the atomization assembly comprising:
   1) a first cover;
   2) a silicone sleeve;
   3) a mouthpiece;
   4) a first silicone ring;
   5) a steel bushing;
   6) a second cover;
   7) a second silicone ring;
   8) an e-liquid container;
   9) a third silicone ring;
   10) a filler plug;
   11) an atomization unit;
the battery assembly comprising:
   12) a positive joint;
   13) a first spring;
   14) a first insulation ring;
   15) a negative pole;
   16) a first fixed part;
   17) a second insulation ring;
   18) a seal ring;
   19) a second fixed part;
   20) a fastener;
   21) a control plate;
   22) a position limiter;
   23) a battery;
   24) a support;
   25) a power button;
   26) a housing;
   27) a second spring; and
   28) a buckle;
wherein:
   the first cover comprises a cavity and the silicone sleeve is disposed in the cavity; the first cover is removably disposed on the mouthpiece; the first silicone ring is sheathed on the mouthpiece; the steel bushing is sheathed on the mouthpiece;
   the mouthpiece is disposed on the second cover; the second silicone ring is sheathed on the second cover; the second cover is disposed on the e-liquid container; the atomization unit is directly connected to the e-liquid container; the third silicone ring is disposed between the e-liquid container and the atomization unit; and the filler plug is disposed on the atomization unit;
   the control plate comprises positive and negative electrodes respectively connected to positive and negative electrodes of the battery; the control plate and the battery are disposed on the support; the position limiter is disposed in the support;
   the first spring is disposed on the positive joint; the positive joint is sheathed on the first insulation ring; the positive joint and the first insulation ring are disposed in the negative pole; the first fixed part is disposed on the negative pole; the seal ring is sheathed on the negative pole; the second insulation ring is sheathed on the second fixed part; the second insulation ring and the second fixed part are disposed on the positive joint; the positive joint is disposed on the support;
   the positive and negative electrodes of the control plate are connected to the positive joint and the negative pole, respectively; the power button is disposed on the housing; the second spring is disposed in a cavity of the buckle; the second spring and the buckle are disposed in the housing; and
   the fastener is disposed on the support; and the support is disposed in the housing.

* * * * *